United States Patent [19]

Hustedt et al.

[11] Patent Number: 5,256,556

[45] Date of Patent: Oct. 26, 1993

[54] PROCESS FOR OBTAINING INVERTASE FROM YEAST

[75] Inventors: Helmut Hustedt; Kay Büntemeyer; Karl-Heinz Kroner; Bernhard Börner, all of Braunschweig, Fed. Rep. of Germany

[73] Assignee: Gesellschaft fur Biotechnologische Forschung GmbH (GBF), Braunschweig, Fed. Rep. of Germany

[21] Appl. No.: 573,222

[22] PCT Filed: May 10, 1990

[86] PCT No.: PCT/EP90/00757

§ 371 Date: Aug. 13, 1990

§ 102(e) Date: Aug. 13, 1990

[87] PCT Pub. No.: WO90/13636

PCT Pub. Date: Nov. 15, 1990

[30] Foreign Application Priority Data

May 12, 1989 [DE] Fed. Rep. of Germany ....... 3915616

[51] Int. Cl.[5] ............................................. C12N 9/26
[52] U.S. Cl. ...................................... 435/201; 435/814
[58] Field of Search ................................ 435/201, 814

[56] References Cited

U.S. PATENT DOCUMENTS

| | | | |
|---|---|---|---|
| 1,689,607 | 10/1928 | Wickenden | 435/201 |
| 1,855,591 | 4/1932 | Wallerstein | 435/201 |
| 1,855,592 | 4/1932 | Wallerstein | 435/201 |
| 1,919,675 | 7/1933 | Wallerstein | 435/201 |
| 1,919,676 | 7/1933 | Wallerstein | 435/201 |
| 1,990,505 | 2/1935 | Wallerstein | 435/201 |
| 2,164,936 | 7/1939 | Miller et al. | 435/201 |
| 3,427,223 | 2/1969 | Frankenfeld et al. | 435/71.2 |
| 3,887,434 | 6/1975 | Frominer et al. | 435/201 |
| 4,278,764 | 7/1981 | Rottighi et al. | 435/144 |
| 4,925,796 | 5/1990 | Bergh et al. | 435/201 |

FOREIGN PATENT DOCUMENTS

| | | |
|---|---|---|
| 2626626 | 12/1977 | Fed. Rep. of Germany . |
| 459824 | 4/1970 | Japan . |
| 2198731A | 6/1988 | United Kingdom . |

OTHER PUBLICATIONS

Cheremisinoff et al., *Biotechnology: Applications and Research*, 1985, pp. 534–546.

*Primary Examiner*—David M. Naff
*Assistant Examiner*—Mike Meller
*Attorney, Agent, or Firm*—Kane, Dalsimer, Sullivan, Kurucz, Levy, Eisele and Richard

[57] ABSTRACT

Invertase is produced by a process wherein, first the yeast cells are disrupted to produce a disrupted cell suspension, second the disrupted cell suspension is adjusted to an acidic pH, third denatured undersired proteins are removed with the cell detritus and lastly the invertase is isolated. The improvement of the invention to the state of the art is that it comprises subjecting the disrupted cell suspension prior to removing the undesired proteins and cell detritus, to a pH of less than 4.5 and to a heat treatment in a continuous thermal denaturation system at a temperature in a range of from 44° C. to about 51° C.

4 Claims, 7 Drawing Sheets

Fig. 1 Acid- and heat-treatment of baker's yeast/invertase 40% suspension, disrupted, pH 4, 50°C Fig. 2 Result of the heat treatment, S.cerevisiae/invertase 4.0% suspension, pH 6, 10 min. (disrupted)

Result of the heat treatment, S. cerevisiae/invertase 40% suspension, pH var., 50 degrees (disrupted)

Acid treatment of brewer's yeast suspension/invertase 20% suspension, disrupted

Fig. 6 Acid treatment of brewer's yeast suspension/invertase with heat treatment 45 degrees/5min, 20% suspension/disrupted Acid treatment of brewer's yeast suspension/invertase with heat treatment 52 degrees/5min., 20 suspension

PROCESS FOR OBTAINING INVERTASE FROM YEAST

BACKGROUND OF THE INVENTION

1. Field of the Invention

The invention relates to methods of preparing invertase from yeast.

2. Brief Description of the Related Art

Invertase is contained within the cells of various yeasts. In order to obtain the enzyme, which is employed on the industrial scale in the foodstuffs industry, it is necessary to disrupt the yeast cells. This is followed by removal of the cell detritus and undesired proteins.

Invertase is distinguished by an above-average resistance to heat and low pH values. Based on this, a process for obtaining invertase has already been proposed, in which a heat treatment is carried out at a pH of 5.0, but this yields a purification factor of only 2. It is therefore not surprising that the method of obtaining invertase in practice does not make use of this process which was proposed as long ago as 1967; N.P. Neumann and J.O. Lampen, Biochemistry 6 (1967), 468–475. On the contrary, the classical working up of invertase provides for two acetone-precipitation steps; cf., for example, Ullmanns Enzyklopädie der technischen Chemie; H. Vetter et al. "Enzyme", in: Ullmanns Enzyklopädie der technischen Chemie, Vol. 10, pp. 475–561 Verlag Chemie, Weinheim, 1975.

A process proposed in a Japanese patent (S. Takai et al., Japan. Patent, JP 45/9824 [70/9824], Apr. 9, 1970) also has a similar procedure:

In this case 30-hour cell lysis and acid treatment at pH 4.5 are followed by filtration and then acetone precipitation and finally extraction. A process proposed by other authors (E. Matulaityte and V. Avizienis, Matr. Biokhim. Konf. Pribalt. Resp. B. SSR, 5th, Volume 2, 14–15, Editor I.K. Sibul Akad. Nauk. Est. SSR: Tallin, USSR) is also very similar to this process.

SUMMARY OF THE INVENTION

The inventors have now re-examined the state of the art, which in the opinion of experts leads no further and has thus been given up, and in doing so have found that surprisingly high purification factors can be achieved and, in addition, clarification is possible more easily by centrifugation when particular measures are taken into consideration. A process for obtaining invertase from yeast is now proposed according to the invention, in which the yeast cells are disrupted, the disrupted cell suspension is subjected in a strongly acid medium to a heat treatment, and the denatured undesired proteins are removed with the cell detritus, preferably by centrifugation, and then the invertase is isolated where appropriate, this process being characterized in that the disrupted cell suspension is subjected at a pH of less than 4.5 to a heat treatment at a temperature in the range from 40° to 60° C., or in that the disrupted cell suspension is subjected to an acid treatment at a pH of less than or equal to 4.0 without heat treatment.

Preferably used in the heat treatment is a temperature in the range from 45° to 50° C. at a pH in the range from 3.0 to 4.2, with a temperature of 48° to 50° C. and the pH range 3.8 to 4.2 being particularly preferred.

Suitable yeasts are brewer's yeast, baker's yeast or yeasts derived therefrom, or microorganisms which contain the genetic information for the production of brewer's yeast invertase or baker's yeast invertase.

It is possible with the process according to the invention to produce virtually particle-free supernatants, for example, in a subsequent centrifugation. Another advantage may be regarded as being the possibility of using virtually no chemicals. The treatment can be carried out with acids approved for foodstuffs, for example phosphoric acid or acetic acid. Undesired concomitant enzymes can be virtually completely inactivated.

DETAILED DESCRIPTION OF THE PREFERRED EMBODIMENTS OF THE INVENTION

Figure 1:
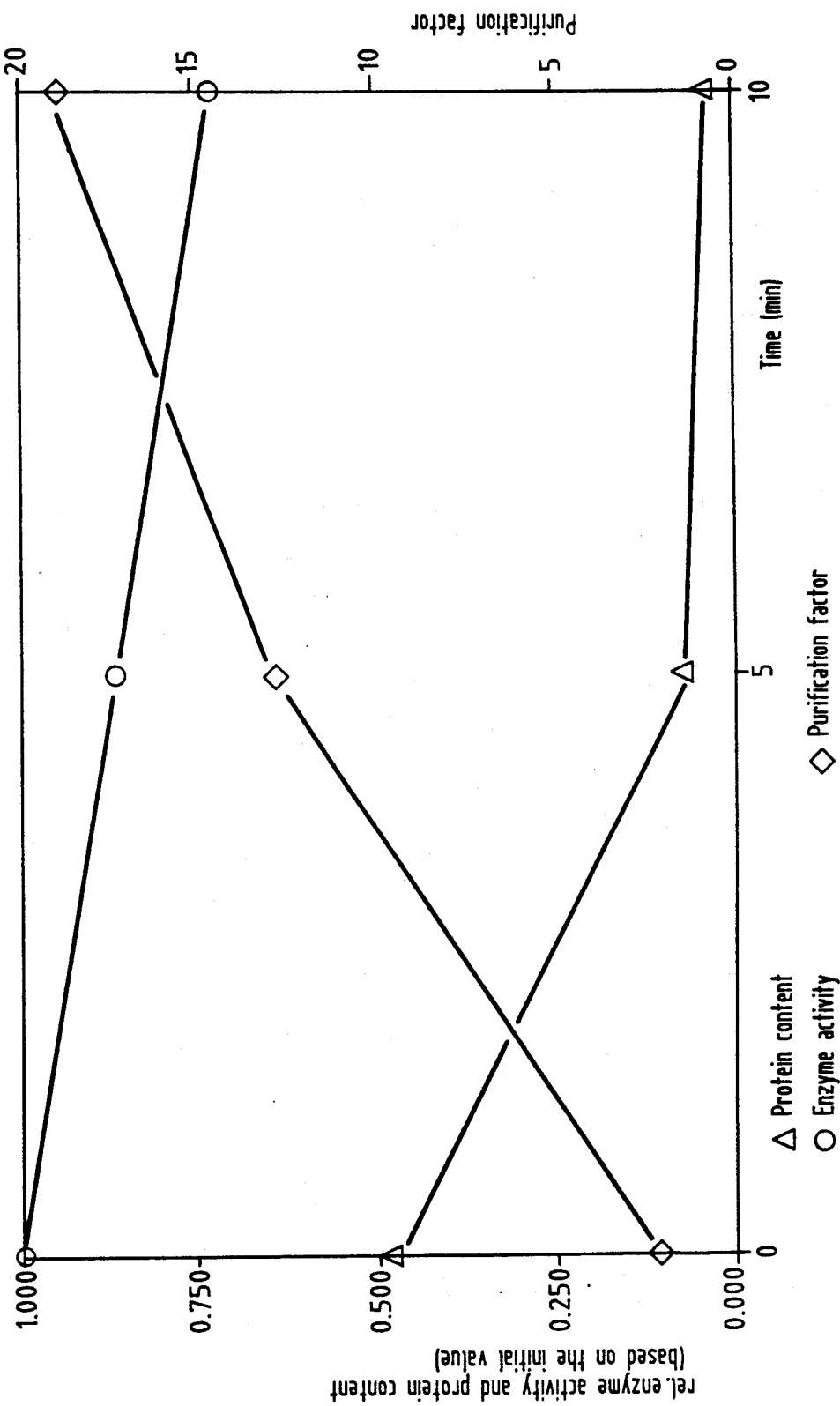
FIG. 1 is a graphical representation of the enzyme activity and protein content of preparations subjected to acid and heat treatment.
Figure 2:
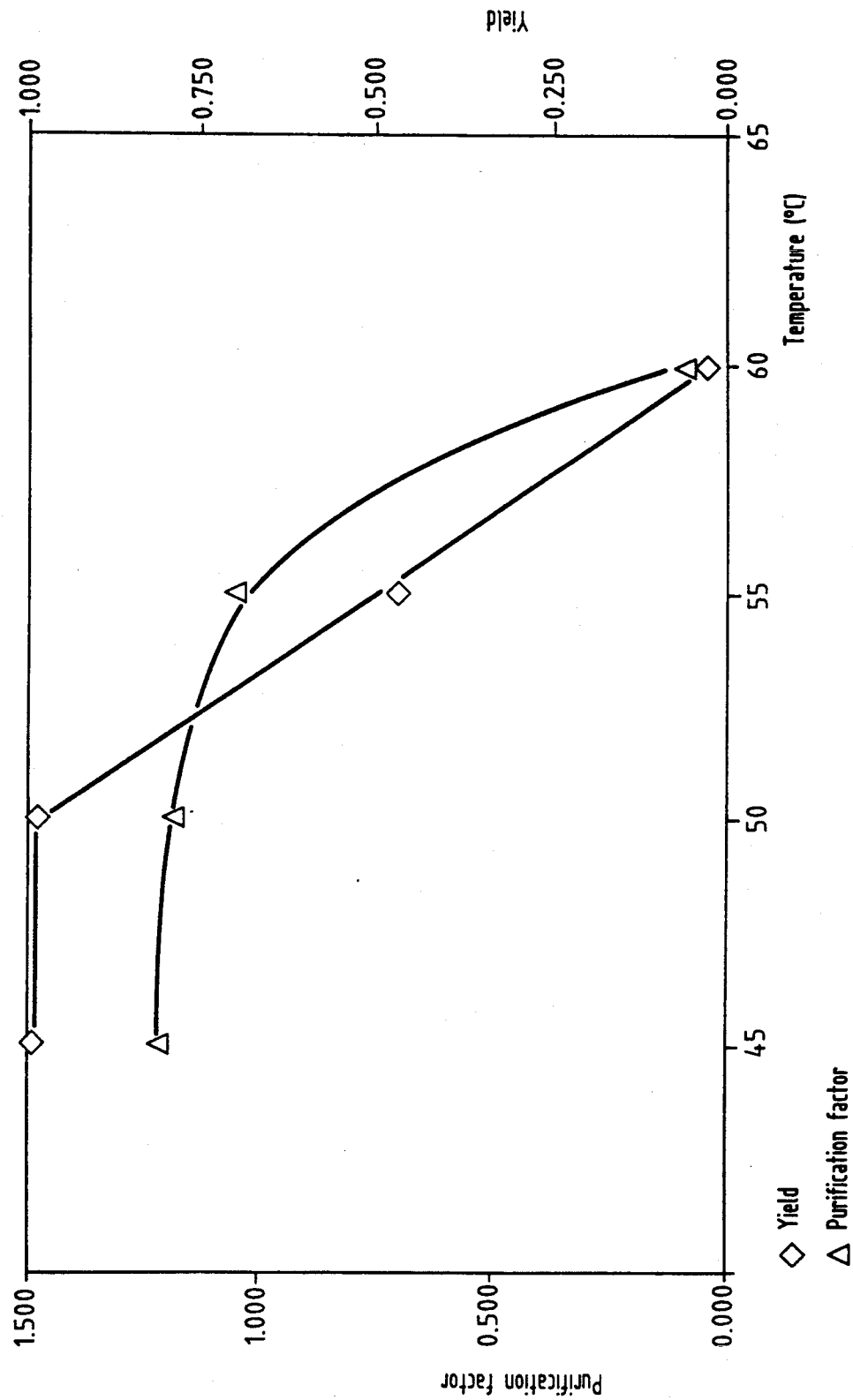
FIG. 2 is a graphical representation of yield and purity of preparations subjected to heat treatment (pH=6.0).
Figure 3:
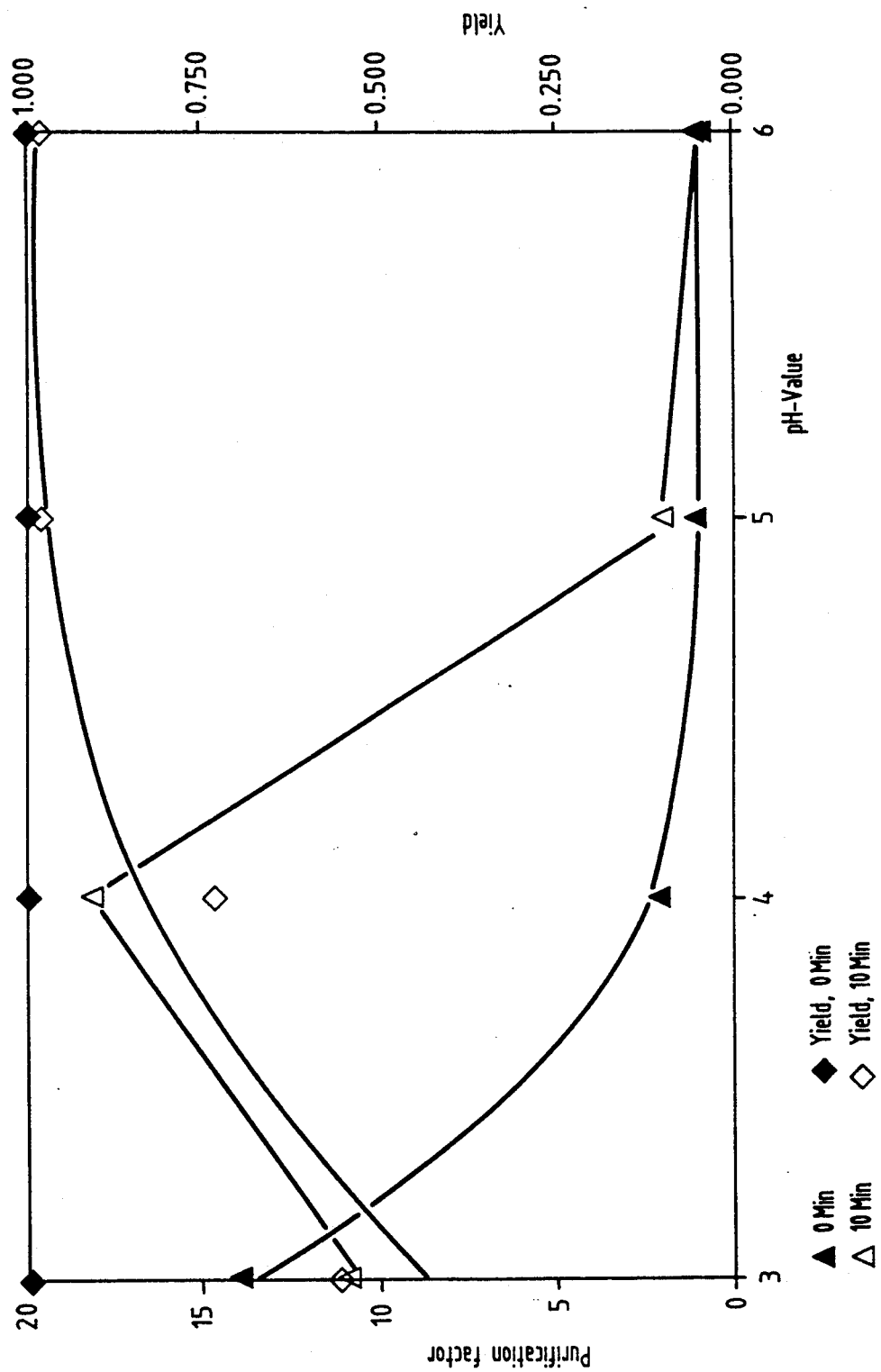
FIG. 3 is a graphical representation of yield and purity of preparations subjected to heat-treatment (various pH).
Figure 4:
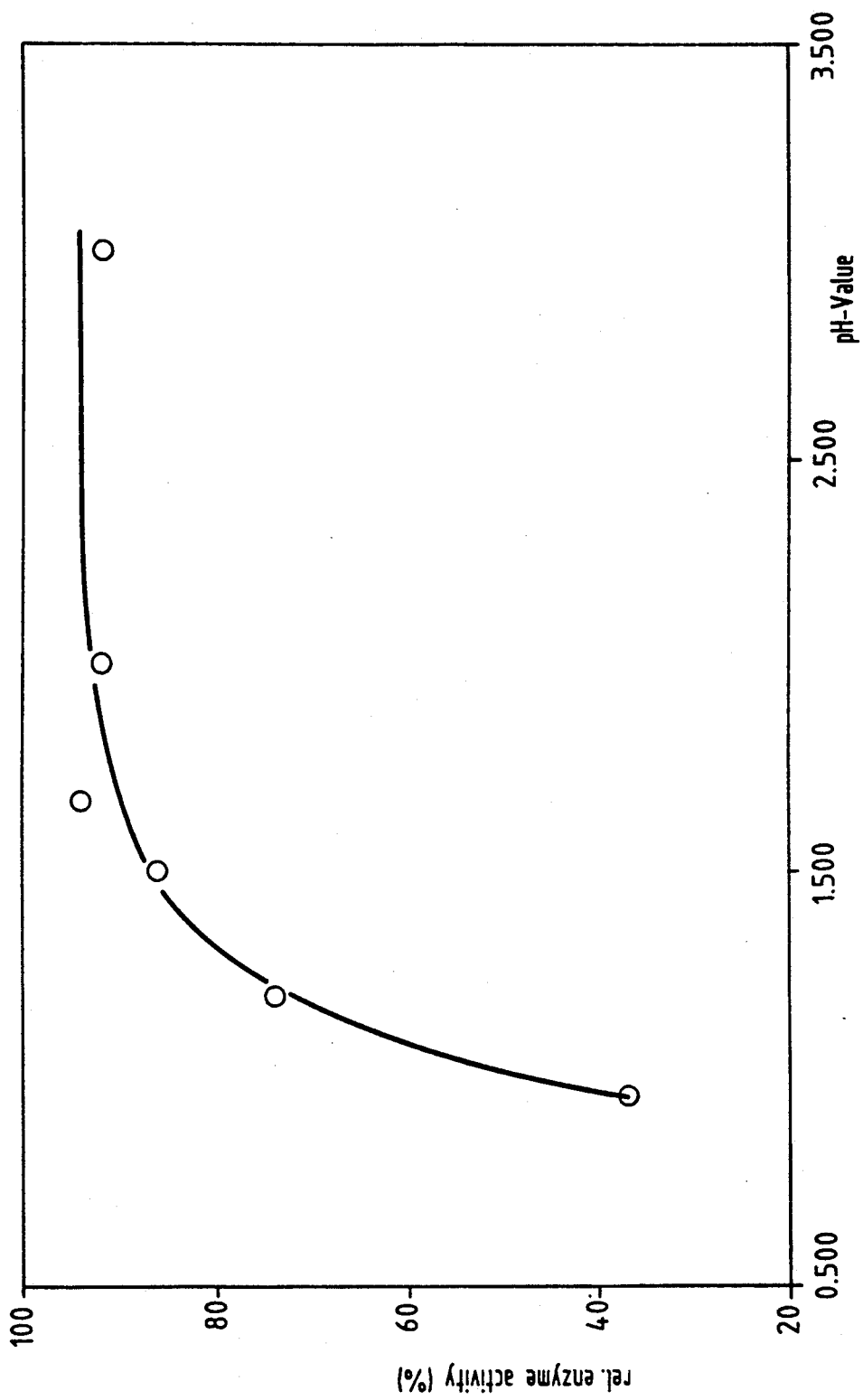
FIG. 4 is a graphical representation of enzyme stability in acid medium.

The invention is explained in more detail by way of example hereinafter.

Starting material

The raw material used was fresh, commercially obtainable baker's yeast (DHW, Northeim) which was supplied in 25 kg bags. The material contained, distributed inhomogeneously, small amounts of kieselguhr which derived from the cell harvest.

Cell disruption

The yeast was suspended in a 1/10 molar dipotassium hydrogen phosphate buffer. The suspension had a pH of approximately 7.25. Disruption was then carried out in a high-pressure homogenizer (Gaulin M 3) until about 75 g of protein had been released per kg moist mass of cells. The disruption was carried out in each case by three passages through the homogenizer at 550 bar. The homogenisate was cooled to about 15° C. in a continuous heat exchanger immediately after leaving the homogenizer.

Acid treatment

The disrupted cell suspension was adjusted to a pH of 4 in each case with phosphoric acid or with acetic acid by titration in a stirred container. The titrated suspension was stirred for about half an hour at a stirrer power of about 4 kW/m$^3$.

Heat treatment

The heat treatment was carried out in a continuous thermal denaturation system, specifically in a static tubular mixer/heat exchanger which ensured rapid and uniform heating with few temperature peaks.

The residence time distribution resulted in a mean treatment time of 10 minutes with a minimum time of 9 minutes and a maximum time of 11 minutes for 70% of the product. In this case, the temperature of the product at the exit from the heater was about 51° C. (0.5° C. standard deviation). In the holding section the product cooled to an exit temperature of 44° C., which was reached after 10 minutes. Cooling to about 15° C. then took place in a second heat exchanger.

Dilution

A 0.05 molar acetate buffer solution was titrated with 2.5 normal potassium hydroxide solution to a pH of 4. This buffer was used to dilute the heat-treated suspension to a content of 10% moist mass of cells.

Centrifugation

The diluted suspension was worked up using a disk separator (1500 m² equivalent clarification area; Westphalia SA-1). Sediment was removed batchwise from the separator, with 17.6% by volume of the suspension being removed as sediment. The enzyme loss in this case was at a similar level. The throughput was 36 l/h.

Ultrafiltration

The separator residue was subjected to an ultrafiltration for concentration. An ultrafiltration unit of polysulfone material with an area of 0.8 m² was used for this. Since invertase has a molecular weight of 270,000 dalton, adequate retention is achieved with an ultrafiltration membrane with a pore size of 1000,000 dalton. With a pressure difference of 1 bar across the membrane and a retentate flow rate of 370 l/h, the average filtrate flow rate achieved was from 60 l/h m² to 75 l/h m². The permeate had an invertase activity of about 3 U/ml, which was equivalent to a 4% loss of product. It was possible with the chosen design of experiment to concentrate the product by a factor of 14.75, with about 50 l of separator supernatant being worked up.

Further details are to be found in Table 1 which follows.

FIGS. 1 to 7 and Table 2 which follow further demonstrate and explain the invention.

TABLE 1

Working up of invertase as described - analytical data on a preparation starting from 5 kg moist mass of cells/baker's yeast

| | Stages | Invertase activity (U/ml) | Process volume (l) | Total activity (10⁶ IU) | Total protein (mg/ml) | Spec. activity (U/mg) | Purification factor | Yield (%) |
|---|---|---|---|---|---|---|---|---|
| 1. | Disruption | about 340 | 10 | 3.4 | 36.4 | 9.3 | 1 | 100 |
| 2. | Acid treatment | " | " | " | 3.1 | 109.7 | 11.8 | " |
| 3. | Heat treatment | " | " | " | 0.5 | 680 | 73 | " |
| 4. | Dilution | about 68 | 50 | " | 0.1 | " | " | " |
| 5. | Centrifugation | " | 41.3 | 2.8 | " | " | " | 82.4 |
| 6. | Ultrafiltration | about 965 | 2.8 | 2.7 | 1.4 | " | " | 79.4 |

TABLE 2 pH stability and concentration of brewer's yeast invertase in the strongly acid range (disruption as 20 percent suspension) without heat treatment

| pH | rel. invertase activity (%) | Concentration factor (approx.) |
|---|---|---|
| 6 | 100 | 1 |
| 4.2 | 95 | 2.6 |
| 3.9 | 92 | 4.5 |
| 3.6 | 87 | 6 |
| 3.3 | 92 | 6 |
| 3.0 | 84 | 6 |
| 2.7 | 84 | 6 |

We claim:

1. In a process for obtaining invertase from yeast, in which the yeast cells are disrupted to produce a disrupted cell suspension, the disrupted cell suspension is adjusted to an acidic pH, and denatured undesired proteins are removed with cell detritus, and then the invertase is isolated, the improvement which comprises subjecting the disrupted cell suspension prior to removing undesired proteins and cell detritus, at a pH of less than 4.5 to a heat treatment in a continuous thermal denaturation system at a temperature in a range of from 44° C. to about 51° C.

2. The process according to claim 1, wherein the disrupted cell suspension is subjected to the heat treatment at a pH in a range from 3.0 to 4.2.

3. The process according to claim 1, wherein the disrupted cell suspension is subjected to a heat treatment at a pH in a range from 3.8 to 4.2.

4. The process according to one of the preceding claims, wherein the yeast is selected from the group consisting of brewer's yeast and baker's yeast.

* * * * *

UNITED STATES PATENT AND TRADEMARK OFFICE
CERTIFICATE OF CORRECTION

PATENT NO. : 5,256,556
DATED : October 26, 1993
INVENTOR(S) : Helmut Husted, et al It is certified that error appears in the above-identified patent and that said Letters Patent is hereby corrected as shown below:

Column 2, line 25; please insert

Figure 5:
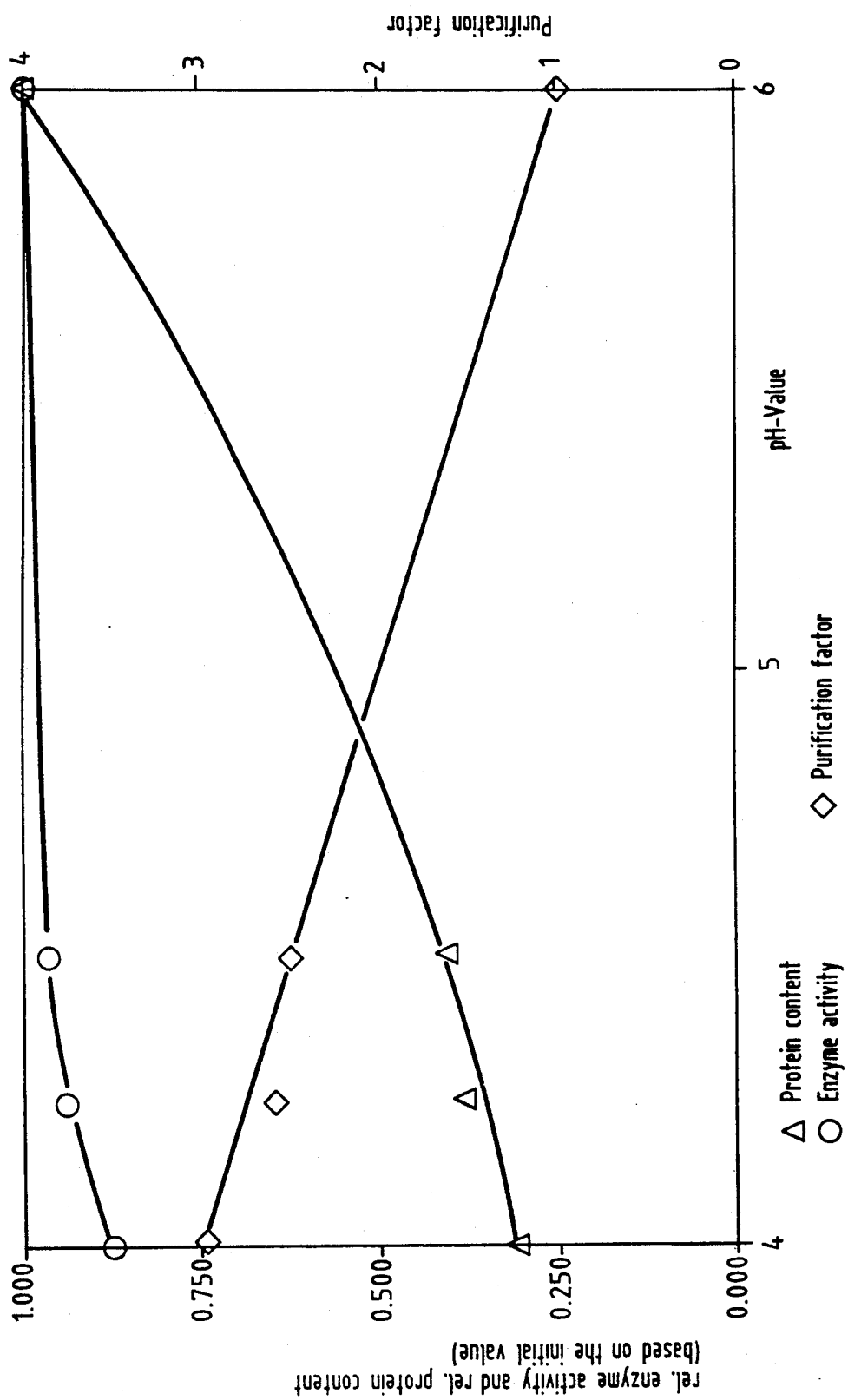
Figure 6:
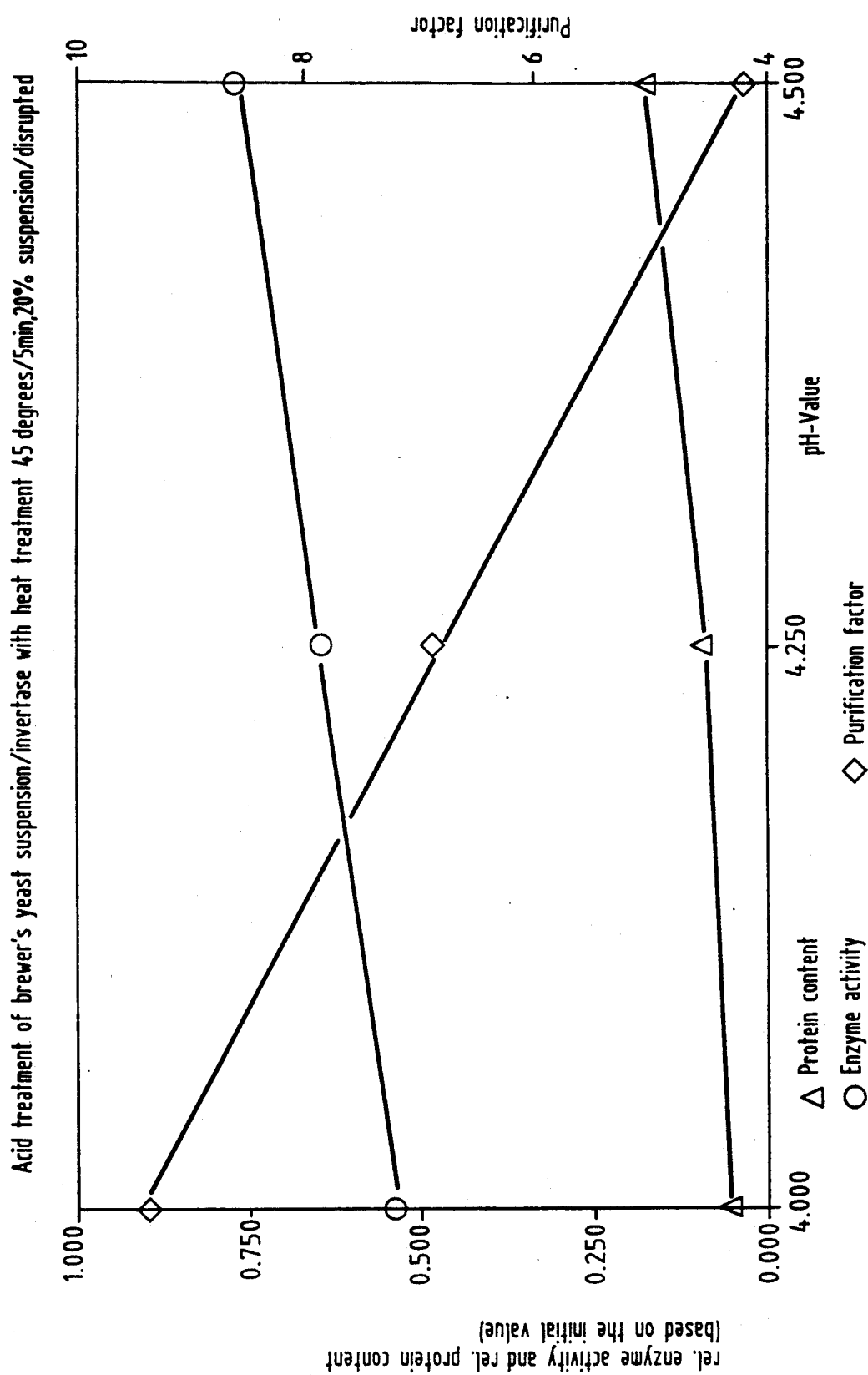
FIG. 6 is a graphical representation of enzyme activity, purity and protein content after preparation with heat treatment.
Figure 7:
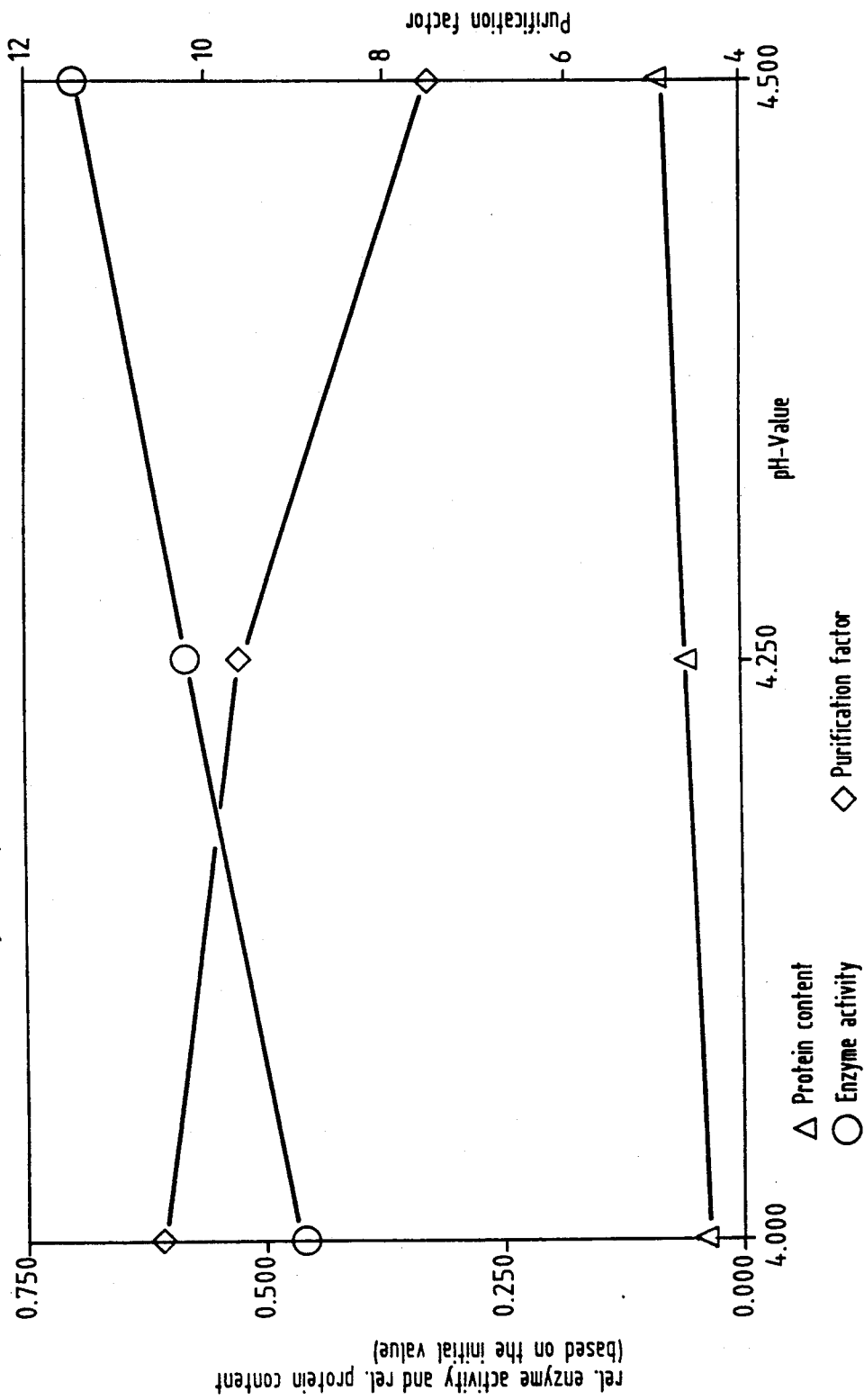
FIG. 7 is a graphical representation of enzyme activity, purity and protein content of preparations made in accordance with the invention.

-- FIG. 5 is a graphical representation of enzyme activity, purity and protein content of preparations according to the invention (Brewer's yeast). --

Signed and Sealed this

Twelfth Day of July, 1994

Attest:

BRUCE LEHMAN

Attesting Officer

Commissioner of Patents and Trademarks